United States Patent

Arnett

[11] Patent Number: 5,851,196
[45] Date of Patent: Dec. 22, 1998

[54] NEEDLE PROTECTOR

[75] Inventor: Jeffery D. Arnett, Ypsilanti, Mich.

[73] Assignee: Vadus, Inc., Toledo, Ohio

[21] Appl. No.: 935,523

[22] Filed: Sep. 23, 1997

Related U.S. Application Data

[63] Continuation of Ser. No. 692,074, Aug. 7, 1996, abandoned.

[51] Int. Cl.⁶ ..................................................... A61M 5/00
[52] U.S. Cl. ........................... 604/110; 604/198; 604/164
[58] Field of Search .................................... 604/198, 192,
604/263, 162, 164, 165, 171, 177, 187,
195, 199, 110

[56] References Cited

U.S. PATENT DOCUMENTS

| | | |
|---|---|---|
| 4,211,741 | 7/1980 | Ostoich . |
| 4,254,773 | 3/1981 | Waldbillig . |
| 4,391,029 | 7/1983 | Czuba et al. . |
| 4,424,833 | 1/1984 | Spector et al. . |
| 4,588,398 | 5/1986 | Daugherty et al. ...................... 604/265 |
| 4,661,300 | 4/1987 | Daugherty . |
| 4,664,657 | 5/1987 | Williamitis et al. .................... 604/265 |
| 4,683,916 | 8/1987 | Raines . |
| 4,713,057 | 12/1987 | Huttner et al. ........................... 604/164 |
| 4,728,322 | 3/1988 | Walker et al. ........................... 604/165 |
| 4,781,703 | 11/1988 | Walker et al. ........................... 604/264 |
| 4,801,295 | 1/1989 | Spencer ................................... 604/199 |
| 4,832,696 | 5/1989 | Luther et al. ........................... 604/164 |
| 4,846,805 | 7/1989 | Sitar ........................................ 604/165 |
| 4,883,699 | 11/1989 | Aniuk et al. . |
| 4,917,669 | 4/1990 | Bonaldo .................................. 604/164 |
| 4,944,728 | 7/1990 | Carrell et al. ........................... 604/164 |
| 4,952,207 | 8/1990 | Lemieux ................................. 604/164 |
| 4,994,034 | 2/1991 | Botich et al. ........................... 604/110 |
| 5,000,740 | 3/1991 | Ducharme et al. ..................... 604/162 |
| 5,019,049 | 5/1991 | Haining ................................... 604/165 |
| 5,051,109 | 9/1991 | Simon ..................................... 604/263 |
| 5,088,985 | 2/1992 | Deras ...................................... 604/192 |
| 5,088,986 | 2/1992 | Nusbaum ................................ 604/195 |
| 5,088,987 | 2/1992 | Noonan, Jr. ............................. 604/195 |
| 5,088,988 | 2/1992 | Talonn et al. ........................... 604/198 |
| 5,092,845 | 3/1992 | Chang ..................................... 604/164 |
| 5,092,853 | 3/1992 | Couvertier, II ......................... 604/195 |
| 5,108,374 | 4/1992 | Lemieux ................................. 604/164 |
| 5,127,905 | 7/1992 | Lemieux ................................. 604/164 |
| 5,135,504 | 8/1992 | McLees ................................... 604/164 |
| 5,137,521 | 8/1992 | Wilkins ................................... 604/263 |
| 5,171,230 | 12/1992 | Eland et al. ............................. 604/250 |
| 5,183,469 | 2/1993 | Capaccio ................................. 604/192 |
| 5,188,597 | 2/1993 | Sweeney et al. ....................... 604/110 |
| 5,188,607 | 2/1993 | Wu .......................................... 604/167 |
| 5,201,713 | 4/1993 | Rosetti .................................... 604/165 |
| 5,215,527 | 6/1993 | Beck et al. .............................. 604/164 |
| 5,215,528 | 6/1993 | Purdy et al. ............................ 604/164 |
| 5,219,333 | 6/1993 | Sagstetter et al. ...................... 604/199 |
| 5,226,899 | 7/1993 | Lee et al. ................................ 604/282 |
| 5,234,416 | 8/1993 | Macaulay et al. ..................... 604/282 |
| 5,240,537 | 8/1993 | Bodicky . |
| 5,242,393 | 9/1993 | Brimhall et al. ......................... 604/86 |
| 5,250,034 | 10/1993 | Appling et al. ........................ 604/164 |
| 5,250,066 | 10/1993 | Lambert ................................. 606/181 |
| 5,254,107 | 10/1993 | Soltesz .................................... 604/282 |
| 5,261,885 | 11/1993 | Lui ......................................... 604/247 |

(List continued on next page.)

*Primary Examiner*—Ronald Stright, Jr.
*Attorney, Agent, or Firm*—Gardner, Carton & Douglas

[57] ABSTRACT

A needle protector having a body, a needle hub and a needle. The body includes a first end and a second end. The body consists of a hollow elongated cylinder defined by a continuous wall having a channel extending between the first and second ends. The continuous wall defines a recess adjacent the first end. The needle hub is movably mounted on the body. The needle hub has an external portion, an internal portion and a tracking member extending between the external portions. The tracking member is positioned in the channel. The external portion includes a single locking arm adapted to be received by the recess and the second end. The needle is mounted in the internal portion of the needle hub. Movement of the needle hub from the first end to the second end results in corresponding movement of the needle into the body until the locking arm engages the second end thereby preventing movement of the needle hub and the needle from the second end to the first end of the body.

6 Claims, 3 Drawing Sheets

U.S. PATENT DOCUMENTS

| | | | |
|---|---|---|---|
| 5,263,942 | 11/1993 | Smedley et al. | 604/110 |
| 5,267,971 | 12/1993 | Brimhall | 604/177 |
| 5,267,979 | 12/1993 | Appling et al. | 604/247 |
| 5,273,543 | 12/1993 | Bell et al. | 604/110 |
| 5,279,591 | 1/1994 | Simon | 604/263 |
| 5,300,048 | 4/1994 | Drewes, Jr. et al. | 604/280 |
| 5,304,136 | 4/1994 | Erskine et al. | 604/110 |
| 5,304,140 | 4/1994 | Kugo et al. | 604/281 |
| 5,304,144 | 4/1994 | Brimhall | 604/177 |
| 5,304,149 | 4/1994 | Morigi | 604/192 |
| 5,304,155 | 4/1994 | Lui | 604/247 |
| 5,306,253 | 4/1994 | Brimhall | 604/165 |
| 5,308,330 | 5/1994 | Grimard | 604/110 |
| 5,312,359 | 5/1994 | Wallace | 604/164 |
| 5,312,361 | 5/1994 | Zadini et al. | 604/165 |
| 5,312,371 | 5/1994 | Dombrowski et al. | 604/198 |
| 5,316,706 | 5/1994 | Muni et al. | |
| 5,318,547 | 6/1994 | Altschieter | 604/198 |
| 5,328,473 | 7/1994 | Fayngold et al. | 604/110 |
| 5,334,144 | 8/1994 | Alchas et al. | 604/68 |
| 5,338,310 | 8/1994 | Lewandowski | 604/192 |
| 5,342,309 | 8/1994 | Hausser | 604/110 |
| 5,344,404 | 9/1994 | Benson | 604/110 |
| 5,344,408 | 9/1994 | Partika | 604/192 |
| 5,356,390 | 10/1994 | Erskine | 604/164 |
| 5,356,395 | 10/1994 | Chen | 604/263 |
| 5,370,624 | 12/1994 | Edwards et al. | 604/169 |
| 5,376,073 | 12/1994 | Graves et al. | 604/86 |
| 5,380,298 | 1/1995 | Zabetakis et al. | 604/265 |
| 5,380,307 | 1/1995 | Chee et al. | 604/264 |
| 5,385,554 | 1/1995 | Brimhall | 604/168 |
| 5,385,555 | 1/1995 | Hausser | 604/192 |
| 5,395,341 | 3/1995 | Slater | 604/164 |
| 5,397,512 | 3/1995 | Sloane, Jr. et al. | |
| 5,405,323 | 4/1995 | Rogers et al. | 604/53 |
| 5,405,326 | 4/1995 | Haber et al. | 604/110 |
| 5,407,431 | 4/1995 | Botich et al. | 604/110 |
| 5,409,461 | 4/1995 | Steinman | 604/110 |
| 5,409,463 | 4/1995 | Thomas et al. | 604/167 |
| 5,409,644 | 4/1995 | Martin et al. | |
| 5,411,486 | 5/1995 | Zadini et al. | 604/198 |
| 5,415,184 | 5/1995 | Peck | 128/880 |
| 5,417,668 | 5/1995 | Setzer et al. | 604/263 |
| 5,419,766 | 5/1995 | Chang et al. | 604/110 |
| 5,419,777 | 5/1995 | Hofling | 604/264 |
| 5,423,758 | 6/1995 | Shaw | 604/110 |
| 5,423,766 | 6/1995 | Di Cesare | 604/192 |
| 5,423,773 | 6/1995 | Jimenez | 604/282 |
| 5,425,712 | 6/1995 | Goodin | 604/96 |
| 5,425,735 | 6/1995 | Rosen et al. | 606/128 |
| 5,425,903 | 6/1995 | Sloane, Jr. et al. | |
| 5,429,613 | 7/1995 | D'Amico | 604/198 |
| 5,429,617 | 7/1995 | Hammersmark et al. | 604/264 |
| 5,435,314 | 7/1995 | Dias | 128/662.06 |
| 5,437,648 | 8/1995 | Graves et al. | 604/263 |
| 5,441,489 | 8/1995 | Utsumi et al. | 604/280 |
| 5,443,457 | 8/1995 | Ginn et al. | 604/280 |
| 5,445,619 | 8/1995 | Burns | 604/192 |
| 5,445,620 | 8/1995 | Haber et al. | 604/110 |
| 5,445,624 | 8/1995 | Jimenez | 604/280 |
| 5,446,230 | 8/1995 | Travers et al. | |
| 5,447,501 | 9/1995 | Karlsson et al. | 604/198 |
| 5,447,503 | 9/1995 | Miller | 604/280 |
| 5,447,724 | 9/1995 | Helmus et al. | |
| 5,449,349 | 9/1995 | Sallee et al. | 604/180 |
| 5,453,095 | 9/1995 | Davila et al. | 604/167 |
| 5,453,099 | 9/1995 | Lee et al. | 604/282 |
| 5,456,668 | 10/1995 | Ogle, II | 604/110 |
| 5,456,674 | 10/1995 | Bos et al. | 604/280 |
| 5,458,658 | 10/1995 | Sircom | 604/192 |
| 5,462,533 | 10/1995 | Daugherty | 604/164 |
| 5,464,398 | 11/1995 | Haindl | 604/280 |
| 5,464,399 | 11/1995 | Boettger | 604/283 |
| 5,472,430 | 12/1995 | Vaillancourt et al. | 604/198 |
| 5,474,539 | 12/1995 | Costa et al. | 604/164 |
| 5,478,313 | 12/1995 | White | 604/110 |
| 5,478,328 | 12/1995 | Silverman et al. | 604/272 |
| 5,487,732 | 1/1996 | Jeffrey | 604/110 |
| 5,498,244 | 3/1996 | Eck | 604/198 |
| 5,520,654 | 5/1996 | Wahlberg | 604/198 |
| 5,651,772 | 7/1997 | Arnett | 604/164 |
| 5,695,476 | 12/1997 | Harris | 604/198 |
| 5,743,882 | 4/1998 | Luther | 604/192 |

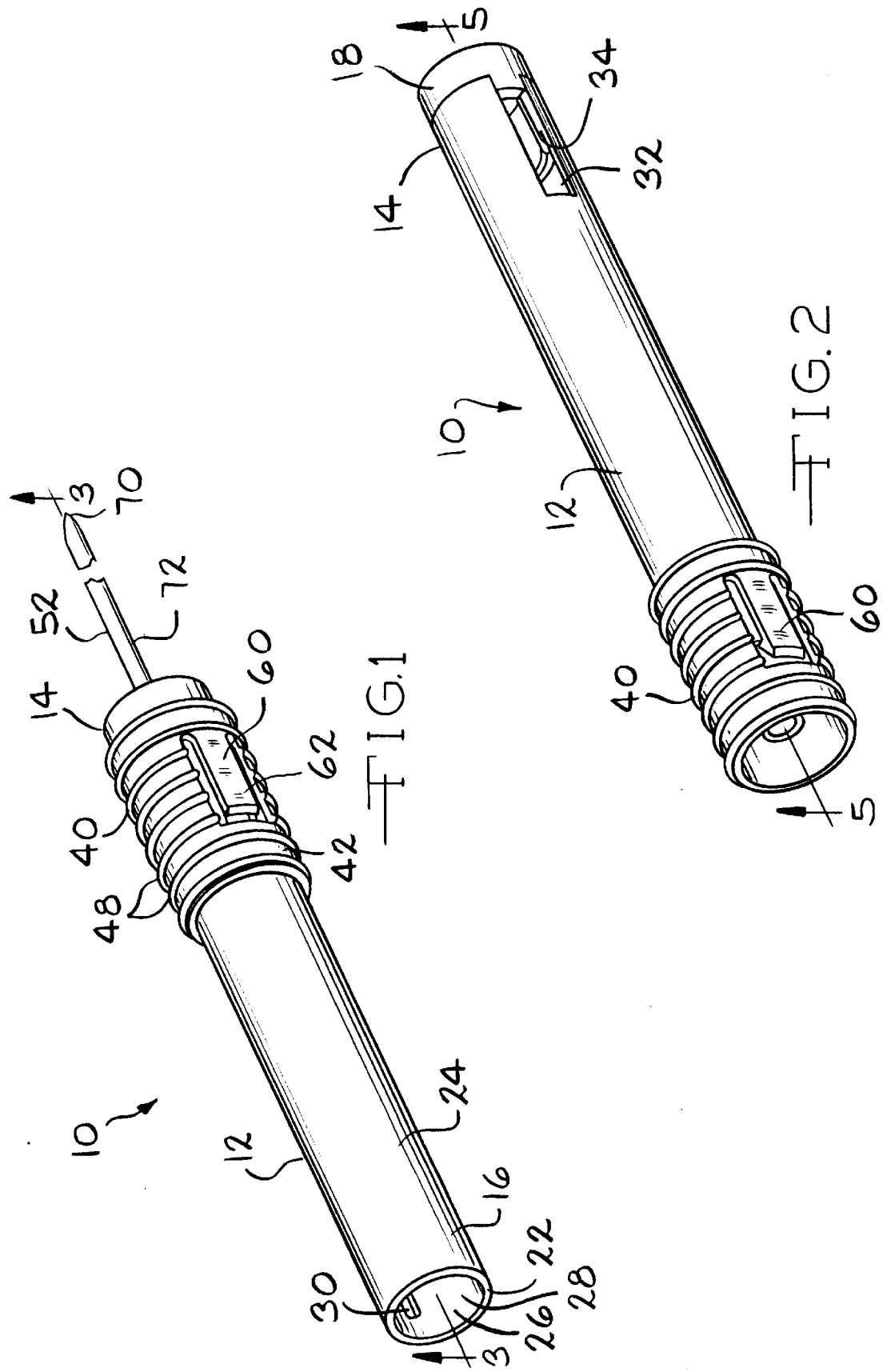

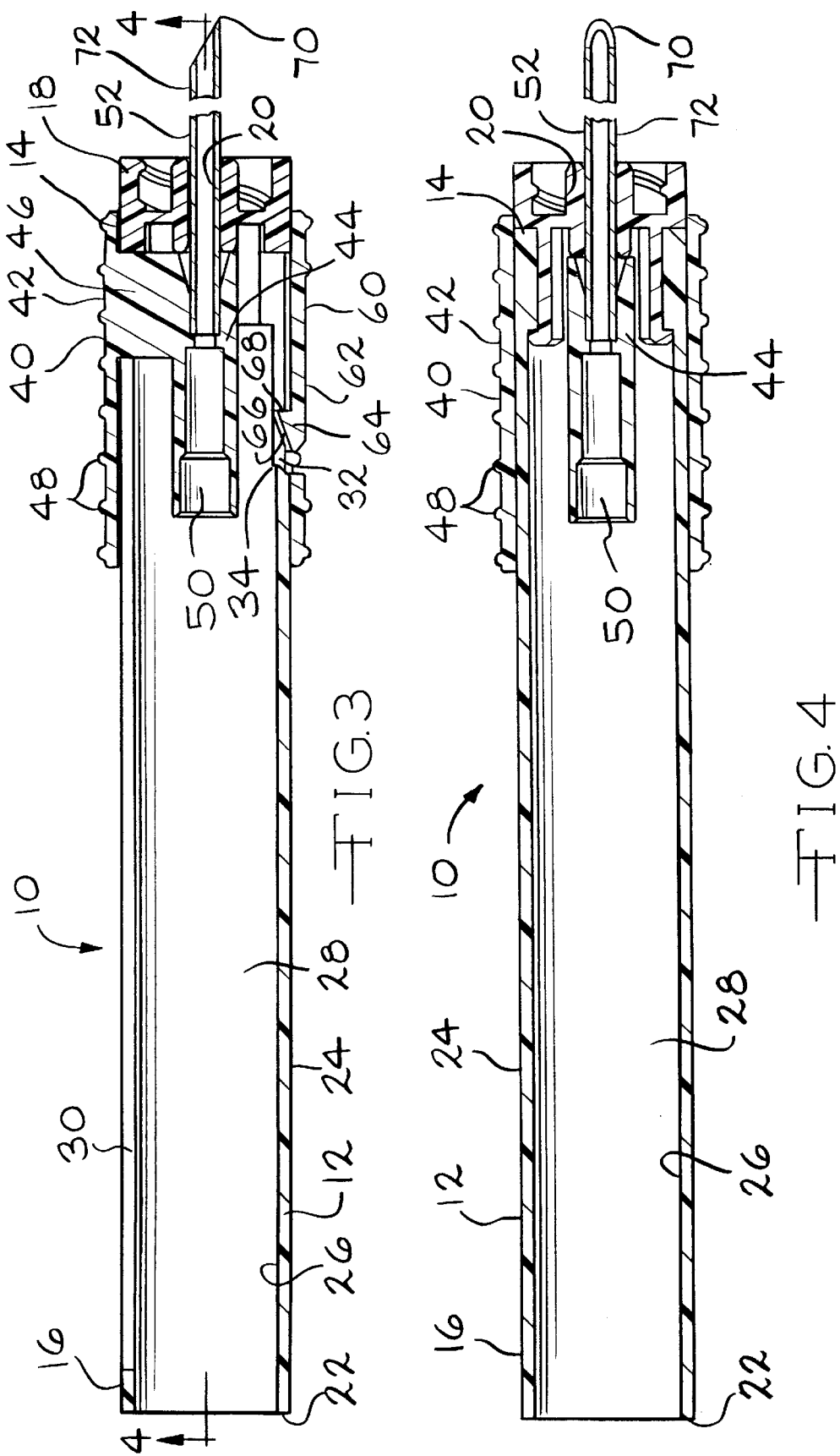

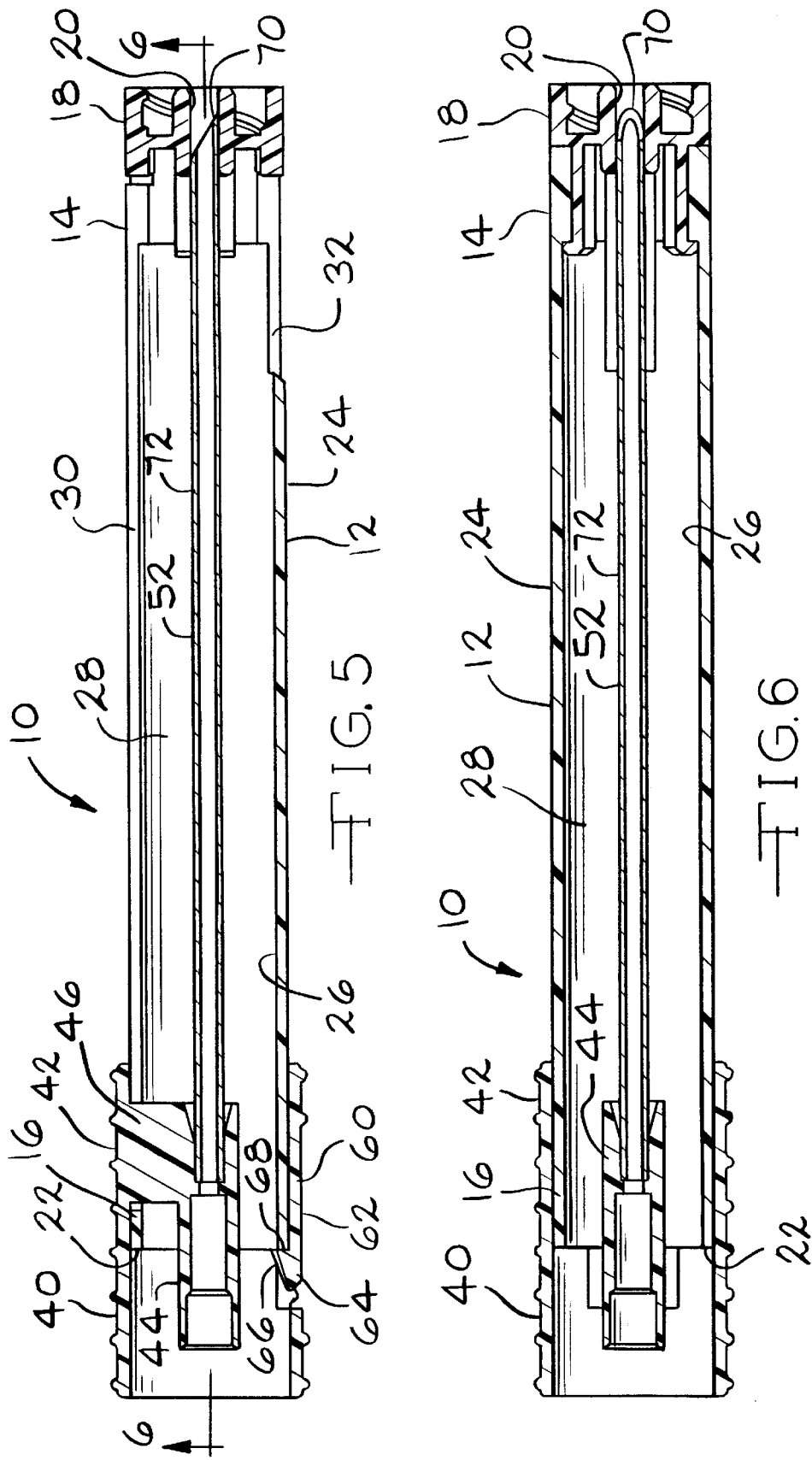

1

NEEDLE PROTECTOR

This application is a continuation of application Ser. No. 08/692,074 filed on Aug. 7, 1996, now abandoned.

BACKGROUND OF THE INVENTION

The present invention relates to a needle protector. More specifically, the invention is directed to a needle protector having a body, a needle hub and a needle. The needle is mounted on the needle hub. When the needle hub is moved along the body, the needle is retracted into the body where it is locked into position.

It has been determined that certain viruses such as the hepatitis B virus can be transmitted from one person to another by accidental "needle-pokes". This type of accident can happen during medical procedures. An example of such a procedure is the insertion of a catheter into a blood vessel with a needle. After the catheter has been inserted in the blood vessel, the needle is removed from the cannula of the catheter at which time the pointed end of the needle can be accidentally poked into the person handling the needle or someone in the vicinity of the needle. The residual blood on the needle can be inserted in the person poked by the needle thereby transmitting a virus in the blood.

It has been found that there is a need for a needle protector in which the needle can be easily handled during insertion in a person and then retracted into the handle and locked into place so that the pointed end of the needle cannot come into contact with another person. The present invention satisfies this need.

SUMMARY OF THE INVENTION

The present invention is directed to a needle protector having, among other things, a body, a needle hub and a needle. The body has a first end and a second end. The body consists of a hollow elongated cylinder defined by a continuous wall having a channel extending substantially between the first and second ends. The continuous wall defines a recess adjacent the first end.

The needle hub is movably mounted on the body. The needle hub has an external portion, an internal portion and a tracking member extending between the external and internal portions. The tracking member is positioned in the channel. The external portion includes a single locking arm adapted to be received by the recess and the second end.

The needle is mounted on the internal portion of the needle hub. Movement of the needle hub from the first end to the second end results in corresponding movement of the needle into the body until the locking arm engages the second end of the body thereby preventing forward movement of the needle hub and the needle from the second end to the first end of the body.

The primary object of the present invention is to provide a needle protector that prevents movement of a needle once the needle has been retracted into the protector.

Other objects and advantages of the present invention shall become apparent to those skilled in the art upon a review of the following detailed description of the preferred embodiment and the accompanying drawings.

BRIEF DESCRIPTION OF THE DRAWINGS

FIG. 1 is a perspective view of a needle protector according to the present invention in which the needle hub is positioned adjacent the first end of the body of the protector;

FIG. 2 is a perspective view similar to the view of FIG. 1 in which the needle hub has been moved adjacent the second end of the body;

FIG. 3 is a cross-sectional view taken along line 3—3 of FIG. 1;

FIG. 4 is a cross-sectional view taken along line 4—4 of FIG. 3;

FIG. 5 is a cross-sectional view taken along line 5—5 of FIG. 2; and

FIG. 6 is a cross-sectional view taken along line 6—6 of FIG. 5.

DETAILED DESCRIPTION OF THE PREFERRED EMBODIMENT

The preferred embodiment and best mode of the present invention will now be described in detail with reference being made to the drawings. The needle protector according to the present invention is indicated generally in the drawings by the reference number "10".

Referring to FIGS. 1, 3 and 4, the needle protector 10 includes a body 12 having a first end 14 and a second end 16. As shown in FIG. 3, the first end 14 is adapted to receive an end cap 18 that defines a needle opening 20 for receiving a needle. The second end 16 includes an end edge 22.

Still referring to FIG. 3, the body 12 consists of a hollow elongated cylinder defined by a continuous wall 24 having an interior surface 26. The interior surface 26 defines a cavity 28. The continuous wall 24 defines a channel 30 that extends longitudinally between the first and second ends 14 and 16. The continuous wall 24 further defines a recess 32 adjacent the first end 14 on the side opposite the channel 30. As shown in FIG. 3, the recess 32 includes a recess edge 34.

Referring to FIGS. 1, 3 and 4, the needle protector 10 includes a needle hub 40 movably mounted on the body 12. As shown in FIG. 3, the needle hub 40 includes an external portion 42, an internal portion 44 and a tracking member 46 that extends between the external and internal portions. The tracking member 46 is positioned in the channel 30. The external portion 42 of the needle hub 40 includes a plurality of circumferencially extending gripping members 48. The gripping members 48 prevent slippage of a user's fingers during use and movement of the needle hub 40. The internal portion 44 of the needle hub 40 defines a chamber 50 for receiving fluid from a needle 52 that is mounted on the internal portion 44. The chamber 50 contains blood and other bodily fluids that flash when the needle 52 is inserted in the tissue of a person.

Referring to FIGS. 1 and 3, the external portion 42 of the needle hub 40 includes a single integral locking arm 60. The locking arm 60 consists of an elongated flexible member 62 that extends longitudinally from the external portion 42 and an inwardly projecting locking member 64. The locking member 64 includes a chamfer 66 adjacent a locking edge 68. When the needle hub 40 is adjacent the first end 14 of the body 12, the locking arm 60 is received by the recess 32.

Referring to FIGS. 1, 3 and 4, the needle 52 includes a pointed end 70 and a hollow shaft 72 that is in communication with the chamber 50 of the internal portion 44. The needle 52 is mounted on the internal portion 44. Therefore, movement of the internal portion 44 results in corresponding movement of the needle 52.

The use of the needle protector 10 will now be described. Referring to FIGS. 1, 2, 5 and 6, when the needle hub 40 is positioned adjacent the first end 14 of the body 12, a portion of the needle 52 is positioned outside the body. When the needle 52 is to be retracted into the body 12, the person operating the needle protector 10 grips the external portion 42 of the needle hub 40 and pulls the external portion from the first end 14 toward the second end 16 of the body 12. As shown in FIG. 3, the chamfer 66 travels over the recess edge 34 to allow the locking arm 60 to travel along the continuous wall 24 of the body 12. The tracking member 46 of the needle hub 40 travels along the channel 30. This causes the needle 52 to enter the cavity 28 of the body 12. When the needle hub 40 is adjacent the second end 1 6, the pointed end 70 enters the needle opening 20 where it is fully contained. As shown in FIG. 5, when the needle hub 40 is adjacent the second end 16, the flexible member 62 of the locking arm 60 causes the locking member 64 to move inwardly so that the locking edge 68 irreversibly engages the end edge 22. This engagement prevents movement of the needle hub 40 and thus the needle 52 from the second end 1 6 to the first end 14. After retraction of the needle 52 into the body 12, the needle protector 10 can be discarded.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

I claim:

1. A needle protector, comprising:

a body having a first end and a second end, said body having a continuous wall defining a channel extending substantially between said first and second ends, said continuous wall defining a recess having a recess edge adjacent to said first end opposite said channel, said continuous wall defining an edge adjacent to said second end;

a needle hub movably mounted on said body, said needle hub having an external portion, an internal portion and a tracking member extending between said external and internal portions, said tracking member positioned in said channel, said external portion including a single locking arm having an elongated flexible member extending longitudinally from said external portion and an inwardly projecting locking member including a chamfer and a locking edge, and wherein said external portion further including a plurality of circumferentially extending gripping members to prevent slippage of a user's fingers during use and movement of the needle hub; and a needle mounted on said internal portion of said needle hub, whereby movement of said needle hub from said first end to said second end results in corresponding movement of said needle into said body until said locking edge of said locking arm irreversibly engages said end edge of said second end thereby preventing movement of said needle from said body;

wherein said external portion circumferentially surrounds said body and said locking arm is located within said recess when said needle hub is at said first end of said body.

2. The invention of claim 1, wherein said internal portion defines a chamber for receiving fluid from said needle.

3. The invention of claim 2 wherein the needle includes a pointed end and a hollow shaft in communication with the chamber.

4. The invention of claim 1, wherein said body is comprised of a substantially hollow elongated cylinder.

5. The invention of claim 1, wherein said first end includes an end cap defining a needle opening for receiving said needle.

6. The invention of claim 1, wherein said locking arm is integral with said external portion.

* * * * *